(12) United States Patent
Keraudren

(10) Patent No.: US 11,250,579 B2
(45) Date of Patent: Feb. 15, 2022

(54) PATIENT MOTION TRACKING SYSTEM CONFIGURED FOR AUTOMATIC ROI GENERATION

(71) Applicant: Vision RT Limited, London (GB)

(72) Inventor: Kevin Keraudren, London (GB)

(73) Assignee: VISION RT LIMITED, London (GB)

( * ) Notice: Subject to any disclaimer, the term of this patent is extended or adjusted under 35 U.S.C. 154(b) by 0 days.

(21) Appl. No.: 16/909,187

(22) Filed: Jun. 23, 2020

(65) Prior Publication Data
US 2020/0402245 A1 Dec. 24, 2020

(30) Foreign Application Priority Data
Jun. 24, 2019 (EP) .................................... 19181918

(51) Int. Cl.
*G06T 7/33* (2017.01)
*G06T 7/38* (2017.01)
*G16H 30/40* (2018.01)
*G06T 7/00* (2017.01)

(52) U.S. Cl.
CPC ............ *G06T 7/337* (2017.01); *G06T 7/0014* (2013.01); *G06T 7/38* (2017.01); *G16H 30/40* (2018.01)

(58) Field of Classification Search
CPC ..... G06T 7/0012; G06T 7/0014; G06T 7/246; G06T 7/248; G06T 7/251; G06T 7/33; G06T 7/337; G06T 7/344; G06T 7/38; G06T 7/50; G06T 7/55; G06T 7/73; G06T 7/74; G06T 7/75; A61N 5/1049; A61N 2005/1059; A61N 5/1064; A61N 5/1069; A61N 5/107; A61N 2005/1072
See application file for complete search history.

(56) References Cited

U.S. PATENT DOCUMENTS

| | | | |
|---|---|---|---|
| 2012/0155731 A1 | 6/2012 | Weersink et al. | ............. 382/131 |
| 2015/0290472 A1 | 10/2015 | Maguire et al. | ...... A61N 5/1039 |
| 2016/0016007 A1 | 1/2016 | Bharat et al. | ........ A61N 5/1037 |
| 2019/0080459 A1* | 3/2019 | Lachaine | ............. A61N 5/1064 |
| 2020/0184625 A1* | 6/2020 | Meir et al. | ............ G06T 15/205 |

* cited by examiner

*Primary Examiner* — Andrew W Johns
(74) *Attorney, Agent, or Firm* — Birch, Stewart, Kolasch & Birch, LLP

(57) ABSTRACT

The present disclosure relates to a patient motion tracking system for automatic generation of a region of interest on a 3D surface of a patient positioned in a radiotherapy treatment room. More particularly, the disclosure relates to an assistive approach of a motion tracking system, by which a region of interest (ROI) is automatically generated on a generated 3D surface of the patient. Furthermore, a method for automatically generating a ROI on the 3D surface of the patient is described. In particular, all the embodiments refer to systems integrating methods for automatic ROI generation in a radiotherapy treatment setup.

20 Claims, 6 Drawing Sheets

PATIENT MOTION TRACKING SYSTEM CONFIGURED FOR AUTOMATIC ROI GENERATION

FIELD

The present disclosure relates to a patient motion tracking system for automatic generation of a region of interest on a 3D surface of a patient positioned in a radiotherapy treatment room. More particularly, the disclosure relates to an assistive approach of a motion tracking system, by which a region of interest (ROI) is automatically generated on a generated 3D surface of the patient. Furthermore, a method for automatically generating a ROI on the 3D surface of the patient is described. In particular, all the embodiments refer to systems integrating methods for automatic ROI generation in a radiotherapy treatment setup.

BACKGROUND

Selecting a Region of Interest (ROI) is an important step in radiotherapy, especially in Surface Guided RadioTherapy (SGRT). The region of interest is the region of the patient's anatomy usually containing the target area for radiation. This ROI is often used for patient positioning and motion tracking monitoring of the patient during positioning and treatment of the patient, respectively. Thus, the region of interest should be clinically relevant, and should preferably be appropriately located with regards to the patient tumour, i.e. concentrated around the target area, which are to be treated with radiation therapy. In a radiation setup, the patient is normally immobilized by a restraining device, such as a head restrain, abdominal restrain, or similar device holding the patient in place on a couch in the treatment room. For the motion tracking to be fast and accurate, the region of interest should preferably exclude such immobilization devices, and thus only contain the target area of the patient. It should also be of appropriate size to ensure reliable surface registration and adequate framerate. Thus, the performance of the patient motion tracking system is dependent on how well a ROI is defined on the patient. The ROI is typically drawn on the patient surface in an imaging software, by the clinician treating the patient.

In existing systems, the user denotes manually the area intended to cover the region of interest, for example with brush strokes or rectangular selections on a screen image of the patient. This manual process of denoting (i.e. drawing up) the ROI on each patient is a time-consuming process, which prolongs the treatment time of each patient undergoing radiotherapy. Further, the clinicians need to have some knowledge and practice in order to draw an optimal ROI for each anatomical site. Different anatomical sites may require different ROIs drawn up, and the ROI and clinicians therefore receive some training in order to know what kind of ROI to use for each anatomical site. Thus, there is a need to provide a simplified solution that addresses at least some of the above-mentioned problems and allows for an optimized process for identifying and marking the ROI of each patient undergoing radiotherapy.

SUMMARY

Accordingly, a simplified patient motion tracking system for automatic generation of a region of interest (ROI) in a 3D surface of a patient is disclosed. In more detail, the disclosure describes systems and methods for automatic generation of a ROI on a 3D surface in an imaging software, based on minimal user input. The patient motion tracking system described in different examples herein is generally configured to track at least a part of a patient during radiotherapy treatment. Especially, the part of the patient being tracked by the system is configured as a region of interest covering a target area (i.e. a cancerous tissue area) of the patient. An accurate estimation and generation of the ROI is important for the accuracy of the motion tracking system, which is why the disclosure more specifically focuses on a system enabling automatic generation of a region of interest on a generated 3D surface of a patient positioned in a radiotherapy treatment room.

Accordingly, in one embodiment, the system comprises a memory comprising stored region of interest (ROI) descriptive data, a 3D surface generation processor configured to utilize an input surface, and to generate a 3D surface from the input surface. The 3D surface preferably comprises at least a target area of the input surface, where the target area is defined as a part of the patient surface where the cancer tissue is concentrated. The system furthermore comprises a ROI generation processor configured to utilize the stored ROI descriptive data and the 3D surface to output a ROI labelled 3D surface to a display and a motion tracking module, wherein the ROI labelled 3D surface is utilized by the motion tracking module to track motion of the patient during positioning and/or treatment of said patient in the treatment room. It should be understood that the "ROI labelled 3D surface" is the 3D surface of the patient having a ROI applied thereto. Thus, the 3D surface is generated by the 3D surface generation processor, then processed and output by the system as a ROI labelled version of the generated 3D surface. Accordingly, by providing a patient motion tracking system, which incorporates a ROI generation processor, a system which is able to automatically generate a ROI on a generated 3D surface is provided for. The automatically generated ROI is utilized by the motion tracking module to ensure that the correct part of the patient is tracked during radiotherapy. Especially the generated ROI on the 3D surface is utilized by the motion tracking module to evaluate if the patient is positioned on a mechanical couch within a set threshold corresponding to where the beam of a radiation therapy apparatus is focused.

In addition to providing accurate motion tracking of the target area, the generation of a ROI on the 3D surface also enables that the amount of data used for motion tracking is limited to the ROI, which ensures fast processing of the motion tracking module.

In an embodiment the system furthermore comprises a 3D scanning reconstruction system enabling the generation of the input surface. It should be noted that the 3D scanning reconstruction system is configured to be arranged in the radiotherapy treatment room in any suitable manner, wherein the 3D scanning reconstruction system is able to record data of the patient lying on e.g. a couch in the treatment room, and transmit such data to the 3D surface generation module. The 3D scanning reconstruction system could be any recording system, which records an input surface of the patient, thus the 3D scanning reconstruction system could be provided as a Kinect system, a structured light system, a LIDAR laser scanning system, a time-of-flight system, a stereo camera system, a Computed Tomography system, a Magnetic Resonance Imaging system.

It should be noted that the input surface could in an embodiment be a CT scan data set, which is input to the 3D surface generation processor. In such cases, the CT scan data obtained of a patient during a CT scan, can be used for generated the 3D surface onto which a ROI is automatically drawn by the system.

In a preferred embodiment, the input surface is configured as a series of 2D image frames of at least the target area of the patient and the 3D surface generation processor is configured to generate from the 2D image frames said 3D surface. Thus, in a preferred embodiment, the 3D scanning reconstruction system is configured as one or more cameras (e.g. one or more pairs of cameras) configured to be arranged in the treatment room and having a field of view covering at least a part of the patient. The 2D images recorded by the cameras are in one embodiment input to the 3D generation processor, which then utilizes the input 2D image frames to generate a 3D surface. Thus, in more detail, the system may comprise one or more cameras configured to be arranged in the radiotherapy treatment room and to obtain said series of 2D image frames of at least the target area of the patient.

In an alternative, the input surface, which are input to the 3D generation processor may also be configured as e.g. CT scan data of a patient, as previously mentioned. Accordingly, in such embodiment, the 3D generation processor may be provided with an input surface configured as a RTSTRUCT DICOM format, namely written to disk as a list of 2D contours, wherein the 3D generation processor utilizes these 2D contours to obtain a 3D surface.

To be able to generate a representative ROI to be automatically overlaid via the ROI generation processor to the 3D surface of the patient, the system may be configured so that the stored ROI descriptive data comprises one or more reference surfaces each having an annotated reference ROI applied thereto. Thus, one or more reference surfaces corresponding to the target area of the 3D surface may be stored in the memory together with corresponding annotated reference ROIs applied onto the reference surfaces. In this way, one or more representative data of a target area of the 3D surface being generated is stored in the memory of the system and utilized by the ROI generator to automatically generate a ROI matching the 3D surface of the input surface. Different possibilities of generating stored reference surfaces and reference ROIs stored in the memory will be explained in detail in the detailed description of the Figures. Thus, it should be noted that the denotation "reference surface" and "reference ROI" covers the data stored in the memory of the system, which in the following are also denoted as "template surface" and "template ROI", In an embodiment, the annotated reference ROI is based on the identification of one or more landmarks applied to each reference surfaces, wherein the landmarks represent uniquely identifiable portions of the reference surface. By providing a set of landmarks, the annotated ROI represents a set of unique features which preferably are to be compared with the 3D surface input to the ROI generation processor, which will become more apparent in the detailed description. It will become apparent in the following that these reference landmarks may denote a set of landmarks applied to a "training set" of reference surface and reference ROIs.

Furthermore, in one embodiment, a set of input landmarks may be annotated onto the 3D surface which are input to the ROI generation processor. These input landmarks may be annotated onto the 3D surface by e.g. a doctor, clinician or similar person treating the patient in the treatment room. Thus, in an embodiment, the 3D surface also contains input landmark information, which may be used in the ROI generation processor as will become apparent in the detailed description. Thus, the disclosure distinguishes between reference landmarks and input landmarks, which are utilized in a "training database" and as input to the ROI generation processor, respectively.

The system described herein can be used for different target ROIs, such as the ROIs generated in relation to treatment of the abdominal part of a patient, the head and neck, the breast etc. No matter what physical part of the patient is to be treated with radiation therapy, a ROI needs to be generated for the target area on the 3D surface of the patient. Thus, for example, when performing Stereotactic Radiosurgery (SRS) it is important that the landmarks of the annotated ROI represents a representative set of data of the head of the patient. Thus, in such embodiment, the input and reference landmarks could be configured as points representing the left and right eyes, the chin and the nose of the patient. For other regions of the patient which is to be treated for cancer, the input and reference landmarks annotated for the ROI is chosen to represent uniquely identifiable points on the target area.

As previously indicated, it is important that the ROI generated by the ROI generation processor is sufficiently covering the target area, wherein the cancer tissue is located. Thus, the system allows for the clinician, doctor etc. to correct and adjust the automatically generated ROI on the 3D surface to ensure that the ROI is sufficiently covering the target area. Thus, to facilitate such adjustment, the ROI labelled 3D surface is configured to be input to a display unit, wherein the display unit is configured to allow the user to adjust the region of interest via control inputs to the ROI generation processor. When providing such control inputs from a user, an adjustment of at least the borders of the ROI label of the ROI labelled 3D surface becomes effective.

As previously mentioned it is also relevant to evaluate the quality of the ROI output from the ROI generation processor, since the performance of the patient motion tracking system is dependent on how well a region of interest (ROI) is defined on the 3D surface of the patient. That is, the ROI should preferably contain a sufficient amount of data for accurate motion tracking of the ROI. Thus, in an embodiment, the system may further be configured so that the quality of the ROI is assessed by an evaluation of the amount of data in the ROI labelled 3D surface. Accordingly, in an embodiment, the ROI labelled 3D surface is read into a quality module of the system, where the quality module is configured to estimate one or more geometric measurement of the 3D data in the ROI labelled 3D surface and to compare the estimated geometric measurement with one or more set thresholds.

In one example, the ROI labelled surface could comprise a plurality of data points, which for a sufficient quality should be configured with a lower than a set threshold.

The geometric measurements should be construed as points/triangles in the ROI labelled 3D surface, angle, curvatures, dimensions, size etc. of the ROI labelled 3D surface. Thus, a suitable measure of the shape, data structure etc. of the ROI is evaluated. In one embodiment, to assess the quality of the ROI, a statistical measurement of the surface curvature may be estimated. In another alternative, the range of the normal of the ROI may be evaluated and compared with a set threshold.

In accordance herewith, the system may thus be configured with a quality module, which reads in the ROI labelled 3D surface, wherein the quality module is configured to estimate the amount of 3D points in said ROI labelled 3D surface and to compare the estimated amount of 3D points with the set threshold. Alternatives as just described can also be used rather than just estimating the amount of points.

Independent of the method of "evaluating" the quality of the ROI, the system is configured to evaluate the quality of the ROI and may output an error message or similar to the user of the system, to indicate that the automatic generated ROI by the ROI generation processor and/or alternatively the adjusted ROI (as adjusted by a clinician) does not contain a sufficient amount of data to be used for motion tracking and/or that the ROI contains too much data for motion tracking. Preferably, the ROI may not contain data, surface, curvature etc. exceeding more than the set threshold, since this may increase the processing time and thus the functionality of the motion tracking.

It should be noted that the ROI generation processor, as previously elaborated on, is configured with a memory, comprising the stored region of interest (ROI) descriptive data. The stored ROI descriptive data may comprise different descriptive information of the ROI and surfaces used for generation of the ROI on the 3D surface. The different descriptive ROI data, which can be utilized in relation to the patient motion tracking system described herein, will be elaborated on in further detail in the following description of the Figures.

BRIEF DESCRIPTION OF DRAWINGS

The embodiments of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each embodiment may each be combined with any or all features of the other embodiment. These and other embodiments, features and/or technical effect will be apparent from and elucidated with reference to the illustrations described hereinafter in which:

DETAILED DESCRIPTION

The detailed description set forth below in connection with the appended drawings is intended as a description of various configurations of the patient motion tracking system. The detailed description includes specific details for providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon application, design constraints or other reasons, these elements may be implemented using electronic hardware, computer program, or any combination thereof.

To set the scene, the current approaches for drawing a ROI on a 3D surface of a patient in a radiotherapy treatment setup will first be elaborated on. Accordingly, current approaches include that a clinician, doctor or other educated person in radiotherapy draw a ROI on the CT scan of the patient. Subsequently the drawn ROI is used to position the patient in the treatment room. Once the patient is in the treatment position, a reference capture of the patient is taken by the patient tracking monitoring system, and the ROI drawn on the CT scan is transferred to the reference capture. Subsequently, the ROI on the reference capture is used for patient monitoring. Thus, the ROI is drawn in a planning stage of the treatment process and is not directly correlated with the actual position of the patient in the treatment room. It should be noted that the ROI may optionally be edited on the reference capture before using the ROI for patient monitoring. Thus, the current methods, known within this field utilize a manual approach, where the clinician, doctor etc. manually draws the relevant region of interest on the target area of the CT scan. This manual process is exactly what the disclosure aims at avoiding in view of providing a more precise and automated approach for ROI generation, which at the same time optimizes the time used on each patient undergoing radio therapy treatment. With these existing methods, risk of errors is introduced to the motion tracking module, when utilizing the ROI drawn on the CT scan rather than on an actual 3D surface generated in e.g. the treatment room, since it is not certain that the patient is positioned on the couch in the treatment room in the exact same position as when the CT scan was captured. Thus, the ROI could have changed, which would have an impact on the accuracy of the motion tracking of the patient considering the target area.

Figure 1:
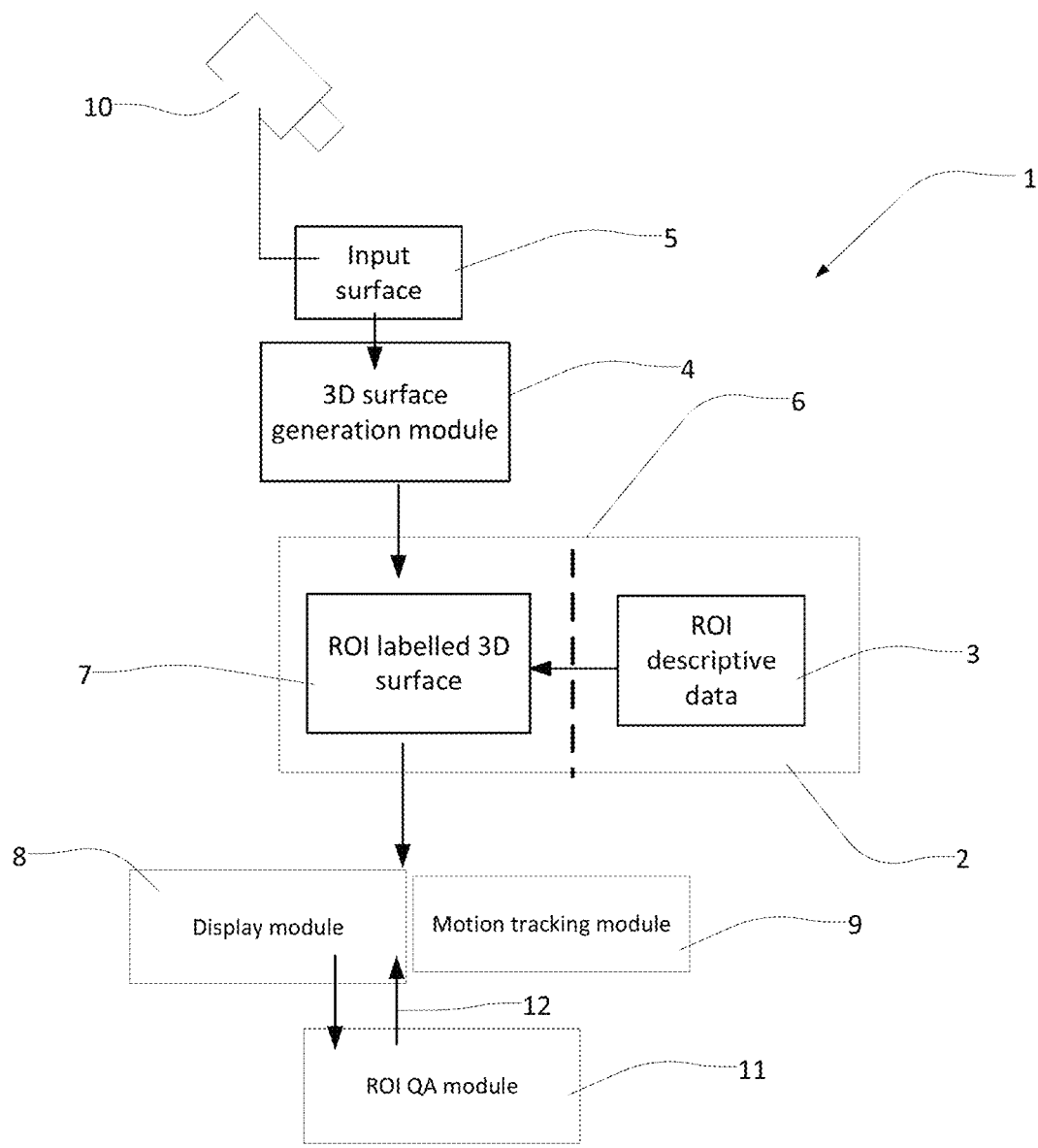
FIG. 1 show a schematic illustration of the patient motion tracking system according to the disclosure.

Accordingly, and with reference to FIG. 1, the disclosure aims at solving these and other problems of the current systems, by providing a patient motion tracking system 1 that is configured for automatic generation of a region of interest on a 3D surface of a patient positioned in a radiotherapy treatment room or alternatively the patient could be positioned in e.g. a CT scanning room (not illustrated in more detail). The patient motion tracking system 1 comprises a memory 2 comprising stored region of interest (ROI) descriptive data 3.

Furthermore, the system comprises a 3D surface generation processor 4 configured to utilize an input surface 5 and generate a 3D surface from said input surface 5, wherein the 3D surface comprises at least a target area of the input surface. The 3D surface is input into a ROI generation processor 6 configured to utilize the stored ROI descriptive data 3 and the 3D surface to output a ROI labelled 3D surface 7 to a display 8 and a motion tracking module 9. In this way, the ROI labelled 3D surface 7 is utilized by the motion tracking module 9 to track motion of the patient during positioning and/or treatment of said patient in the treatment room.

The illustration according to FIG. 1, shows that the memory 2 may form part of the ROI generation processor 6. However, it should be noted that the memory is not necessarily part of this specific part of the system 1 but could be stored anywhere in the patient motion tracking system.

As further illustrated in FIG. 1, the system 1 comprises a 3D scanning reconstruction system 10 configured to be arranged in the radiotherapy treatment room and configured to generate the input surface 5. As explained in the summary part, the 3D scanning reconstruction system can be a camera, such as e.g. a stereoscopic camera, it may be a system like a Kinect setup, or any other suitable system that creates a data stream from which a 3D surface can be generated.

In embodiments of the system, which is not illustrated in further detail, the input surface 5 may be configured as a series of 2D image frames of at least the target area of the patient. Thus, the input surface 5 may be generated in any suitable manner as an "image" or similar "reconstruction data" of the patient, where these data are input to the 3D surface generation processor that generates, from the 2D image frames or other suitable reconstruction data, the 3D surface. In a preferred embodiment, the input surface is a set of 2D images captured from a camera, such as one or more stereoscopic cameras, mounted in the treatment room.

In alternative embodiments, the input surface, may as previously explained be configured as CT scan data of the patient, wherein the scan data have been obtained in a pre-planning phase of the radiotherapy treatment. When utilizing the CT scan data as the input surface, the 3D generation processor is configured to generate a 3D surface from the CT scan data. The CT scan data would in this embodiment, not contain a previously generated ROI, but would be configured as the RAW CT scan data.

In a further alternative, the input surface may be configured as data received from a LIDAR sensor in the form of a point cloud, to which a 3D surface can be fitted.

In the preferred embodiment of utilizing one or more cameras mounted in the treatment room, the cameras are configured to obtain a series of 2D image frames of at least the target area of the patient. Furthermore, these 2D cameras, are after the automatic generation of the ROI on the 3D surface configured to capture, continuously during treatment, 2D image streams of the patient lying on the couch. The 2D image streams are input to the motion tracking module and utilized together with the ROI labelled 3D surface to track any potential motion of the patient by comparing the ROI labelled 3D surface with a 3D surface generated based on the continuous receival of the 2D image streams by the motion tracking module.

In more detail, the stored ROI descriptive data comprises one or more reference surfaces each having an annotated reference ROI applied thereto. The details of the reference surfaces and reference ROIs will become more apparent when describing the more specific embodiments concerning the ROI descriptive data in the following. Furthermore, the annotated reference ROI may be based on the identification of one or more reference landmarks applied to each of reference surfaces, wherein the reference landmarks represent uniquely identifiable portions of the reference surface. Thus, it should be noted that two different sets of landmarks can be utilized in the following example embodiments. In some embodiment's only landmarks (i.e. reference landmarks) are applied to the reference ROIs stored in the memory as ROI descriptive data. However, in other embodiments, also in addition to the reference landmarks, a set of input landmarks can be applied to the 3D surface input to the ROI generation processor.

As illustrated schematically in FIG. 1, the ROI labelled 3D surface 7 is configured to be input to the display unit 8, wherein the display unit is configured to allow the user to adjust the region of interest via control inputs to the ROI generation processor. Accordingly, the control inputs from the user, utilizes an adjustment of at least the borders of the ROI label of the ROI labelled 3D surface 7.

As further illustrated in FIG. 1, the system 1 may further comprise a ROI quality module 11. The ROI quality module 11 is configured to take as input the ROI labelled 3D surface 7 and evaluate the quality of a ROI label forming part of the ROI labelled 3D surface 7. In more detail, the ROI labelled 3D surface 7 is read into the ROI quality module 11 which then estimates geometric measurements of the 3D data in the ROI labelled 3D surface 7, such as size or curvature, and compare the estimated measurements with set thresholds. The size of the threshold may be set on the basis of the amount of data contained within the ROI label of the ROI labelled surface, namely the size of the ROI labelled surface Alternatively, the size of the threshold could be based on a percentage measure between a reference data amount needed for the ROI labelled 3D surface to be used for motion tracking and the actual amount of data in the generated ROI labelled 3D surface. In any case, it is important that the set threshold reflects that the ROI labelled 3D surface is within a maximum value for a ROI, beyond which the impact on the framerate becomes too important. In the context of the ROI quality module, it is more specifically in an embodiment, checked that the ROI has less than 10000 triangles (alternative points, curvature, normal etc), in order to say it is an acceptable ROI. The reasoning behind choosing a set threshold that is less than a maximum value for a ROI labelled 3D surface, is due to the fact that a too large ROI labelled 3D surface is unlikely to be clinically relevant, and such large surface will also slow down the software and hinder the monitoring of the patient. Accordingly, the threshold for the quality of the ROI 3D labelled surface should be set to balance the pros and cons of providing the motion tracking system with sufficient amount of data to accurately monitor and track the patient, while at the same time being within a data-limit not slowing down the processing performed by the software of the motion tracking module. In an alternative, geometric measurements, such as surface curvature, can be compared to set thresholds to ensure that the selected ROI contains sufficient geometrical details for the performance of the motion tracking system.

When the ROI 3D labelled surface have been evaluated by the ROI quality module, the ROI quality module is configured to output an evaluation to the user, which evaluation is configured as one of two or more outcomes. In one scenario, the ROI quality module outputs to the user an indicator that the ROI labelled 3D surface is appropriate for motion tracking, or in another scenario, the ROI quality module outputs to the user an indicator that the ROI labelled 3D surface should be adjusted to create a more appropriate 3D labelled ROI surface for motion tracking. Thus, the ROI quality module is configured to feedback (illustrated as the arrow 12) to the display module if the ROI labelled 3D surface is approved for further motion tracking. It should be noted that in an embodiment, only when the 3D labelled ROI surface have been "approved", i.e. evaluated to be appropriate for motion tracking by the quality module 8, is the ROI labelled 3D surface input to the motion tracking module 9. This ensures that the ROI labelled 3D surface contains the correct amount of data needed for accurate motion tracking.

Figure 2:
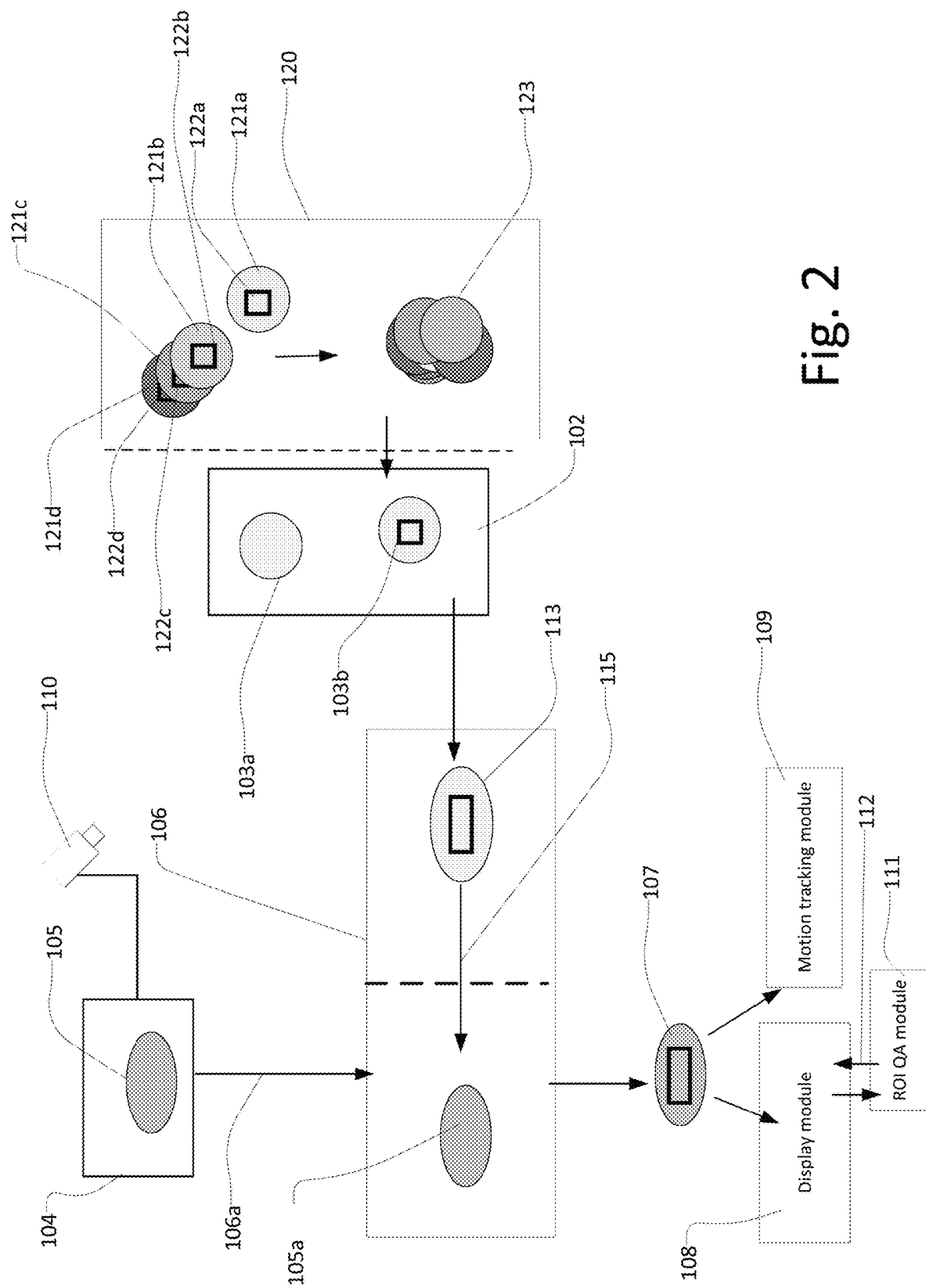
FIG. 2 show a schematic illustration of the patient motion tracking system according to an example for automatic generation of a ROI on a 3D surface.

Referring now to FIG. 2, an example of an embodiment of the ROI generation processor 106 is illustrated in more detail. In this embodiment, the ROI generation processor 106 is as in the general setup previously described configured to take as input a 3D surface of a patient lying on a couch in the treatment room. The 3D surface is as previously described generated from an input surface 105, which are input to a 3D surface generation processor 104 of the system 1. Further, the input surface 105 is obtained by one of a chosen 3D reconstruction system 110, such as one or more cameras. Thus, it should be apparent that several features of the system described in the embodiment of FIG. 1 is similar to those of the embodiment in FIG. 2, Therefore, only the main differences will be explained in detail. The generated 3D surface is illustrated in FIG. 2 as a surface 105a, which is input to the ROI generation processor from the 3D surface generation module 104 (the input path illustrated by an arrow 106a).

In the embodiment of FIG. 2, the ROI generation processor 106, comprises a memory 102 which is configured with ROI descriptive data 103a, 103b. The ROI descriptive data 103a, 103b, is in more detail configured as a template surface 103a and a template ROI 103b, wherein the template surface 103a and template ROI 103b is configured to be input to the ROI generation processor 106. Thus, the memory 102 can form part of the ROI generation processor 106 and/or be a separate unit in the system. Furthermore, the template surface 103a and template ROI 103b can be constituted as a reference surface and a reference ROI in this embodiment.

The ROI generation processor 106, is configured to align and warp the template ROI 103b and template surface 103a with the 3D surface 105a to create at least a warped ROI 113, and subsequently to transfer (indicated by arrow 115) said warped ROI 113 to said 3D surface 105a, as illustrated in FIG. 2.

Furthermore, as illustrated in FIG. 2, the system may also comprise a training module 120, which is configured to generate and output to the memory 102, the template surface 103a and the template ROI 103b. Thus, the training module 120 may form part of the system, but could also be utilized as a separate component, which are remote from the system as such. In any case, the training module 120 is used to generate a representative data set of a ROI, comprising the stored template ROI 103b and template surface 103a, describing how a ROI on an example target surface (i.e. the 3D surface) could look like.

Therefore, in an embodiment, the system may, as illustrated in FIG. 2 comprise the described training module 120, which comprises two or more reference surfaces 121a, 121b, 121c, 121d each having an annotated reference ROI 122a, 122b, 122c, 122d applied thereto. The training module is configured to align 123 the two or more reference surfaces 121a, 121b, 121c, 121d and subsequently to calculate an average of the aligned reference surfaces to produce the template surface 103a. Furthermore, the training module is also configured to calculate an average of the annotated ROIs 122a, 122b, 122c, 122d to produce the template ROI 103b. The produced template ROI 103b and template surface 103a is then stored in the memory of the system and are subsequently used as previously described in the ROI generation processor 106 to generate a ROI labelled 3D surface 107. The generation of the ROI labelled 3D surface 107 is as described above. As also described in relation to FIG. 1, this ROI labelled 3D surface 107 is output to a display module 108 and/or a motion tracking module 109, which then utilizes the ROI labelled 3D surface 107 for motion tracking of a patient in a radiotherapy treatment setup. In addition, as described in the general embodiment of FIG. 1, the system in this embodiment also comprises a similar quality module 111, which feedback 112 and evaluation of the generated ROI back to the user via the display module 108.

Figure 3:
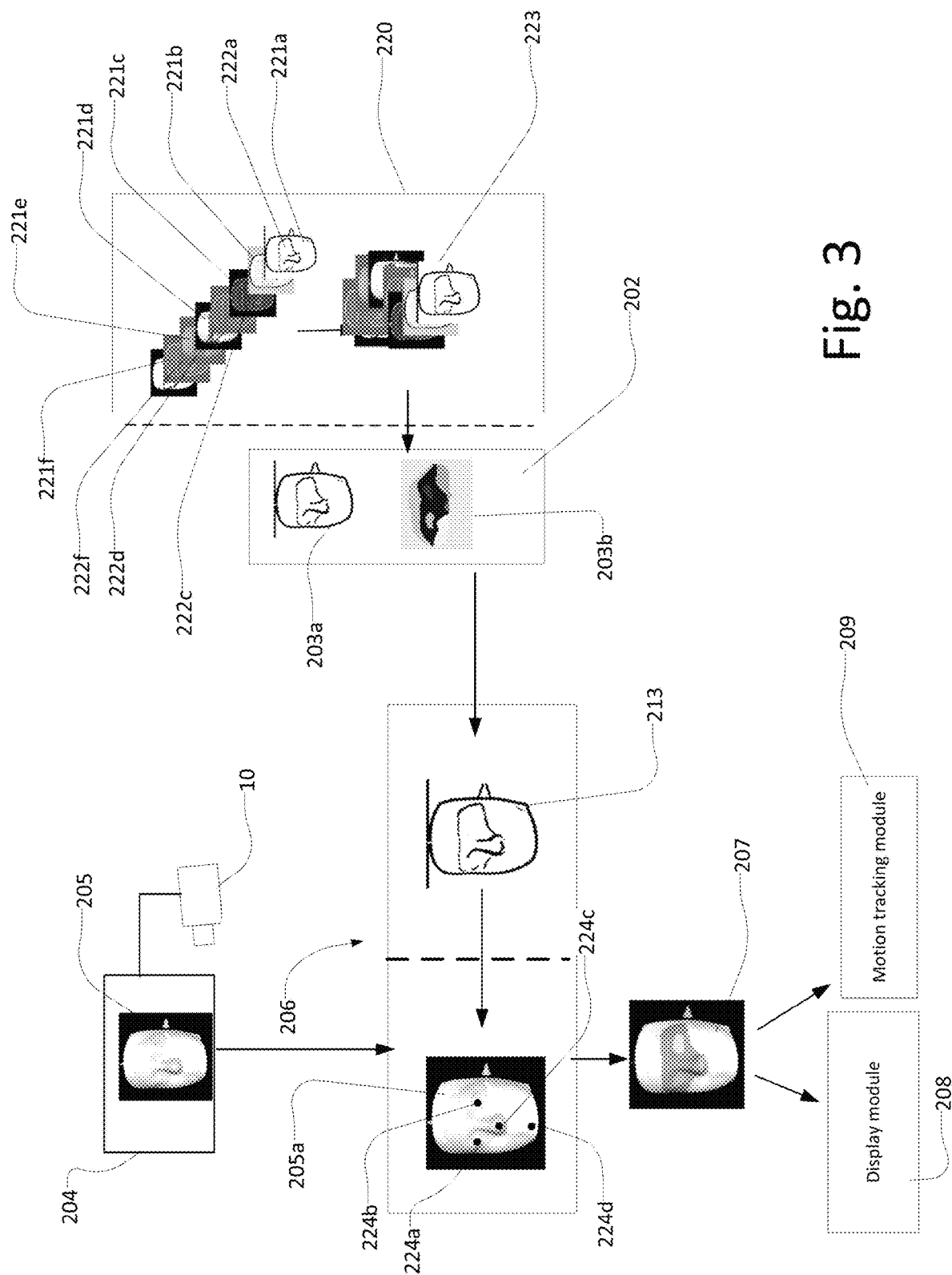
FIG. 3 show a schematic illustration of the patient motion tracking system according to the first example for automatic generation of a ROI on a 3D surface, especially in a stereotactic radiosurgery setup.

Referring now to FIG. 3, a more illustrative example of substantially the same system as described in relation to FIG. 2 is shown. The embodiment shown in FIG. 3 illustrates the system configuration in a stereotactic radiosurgery treatment situation. In this situation, the treatment is concentrated on treating regions of the brain. In such system the patient is initially positioned on a couch in the treatment room, where a head mask or similar head restrain is utilized to immobilise the patient. In such treatment, the region of interest to be tracked by the motion tracking module is preferably concentrated around the facial part of the patient. Thus, in the example shown, the data used for 3D surface generation is configured as 3D reconstruction images (also denoted input surface 205) of the patient lying on the couch, such as camera (denoted 10) images and/or CT scan data, from which the 3D surface generator 204 is configured to generate a 3D surface 205a of the face of the patient lying on the couch. This 3D surface 205a is input into the ROI generation processor 206, which utilize in the same manner as described in relation to FIG. 2, a template surface 203a and a template ROI 203b stored in a memory 202, to generate a ROI labelled 3D surface 207 of the patient. The template ROI 203a and template surface 203b is generated in the same way as previously described in relation to the training module 120 of FIG. 2. Thus, in the embodiment shown in FIG. 3, the same features of the training module 120 in FIG. 2 has been given the same numerals with a 100 added thereto.

It should be noted that in both described embodiments of FIG. 2 and FIG. 3, the template ROI 203b may be produced from annotations of reference landmarks onto the surface of a plurality of the different reference surfaces 221a, 221b, 221c, 221d, 221e, 221f, of the training module 220. Thus, the reference surfaces 221a of the training module 220 may comprise annotated landmarks, which defines the ROIs 222a, 222f, 222d, 222c of each of the reference surfaces. In this way, the template ROI 203b of the template surface 203a similarly comprises reference landmarks which are based on an averaging and alignment 223 of the reference surfaces and reference ROIs in the training module.

In an embodiment, the reference landmarks are utilized together with a set of input landmarks 224a, 224b, 224c, 224d defining markers of the 3D surface 205a of the patient. Accordingly, the system may prompt the user with the option of denoting one or more input landmarks 224a, 224b, 224c, 224d onto the 3D surface 205a, which is then used by the ROI generation processor 206 to align and warp 213 at least the template ROI 203b to the 3D surface 205a, thereby generating the ROI labelled 3D surface 207.

In the specific example of the SRS setup, as just described, the reference and input landmarks may be configured as points representing the left and right eyes, the chin and the nose of the patient, as illustrated by the black dots 224a, 224b, 224c, 224d in FIG. 3.

Furthermore, the ROI labelled 3D surface 207 is as previously described input to a display module 208 and to a motion tracking module 209. In addition, even though not shown, is should be contemplated that the embodiment of FIG. 3 also comprises the quality module as explained in relation to FIG. 1.

Figure 4:
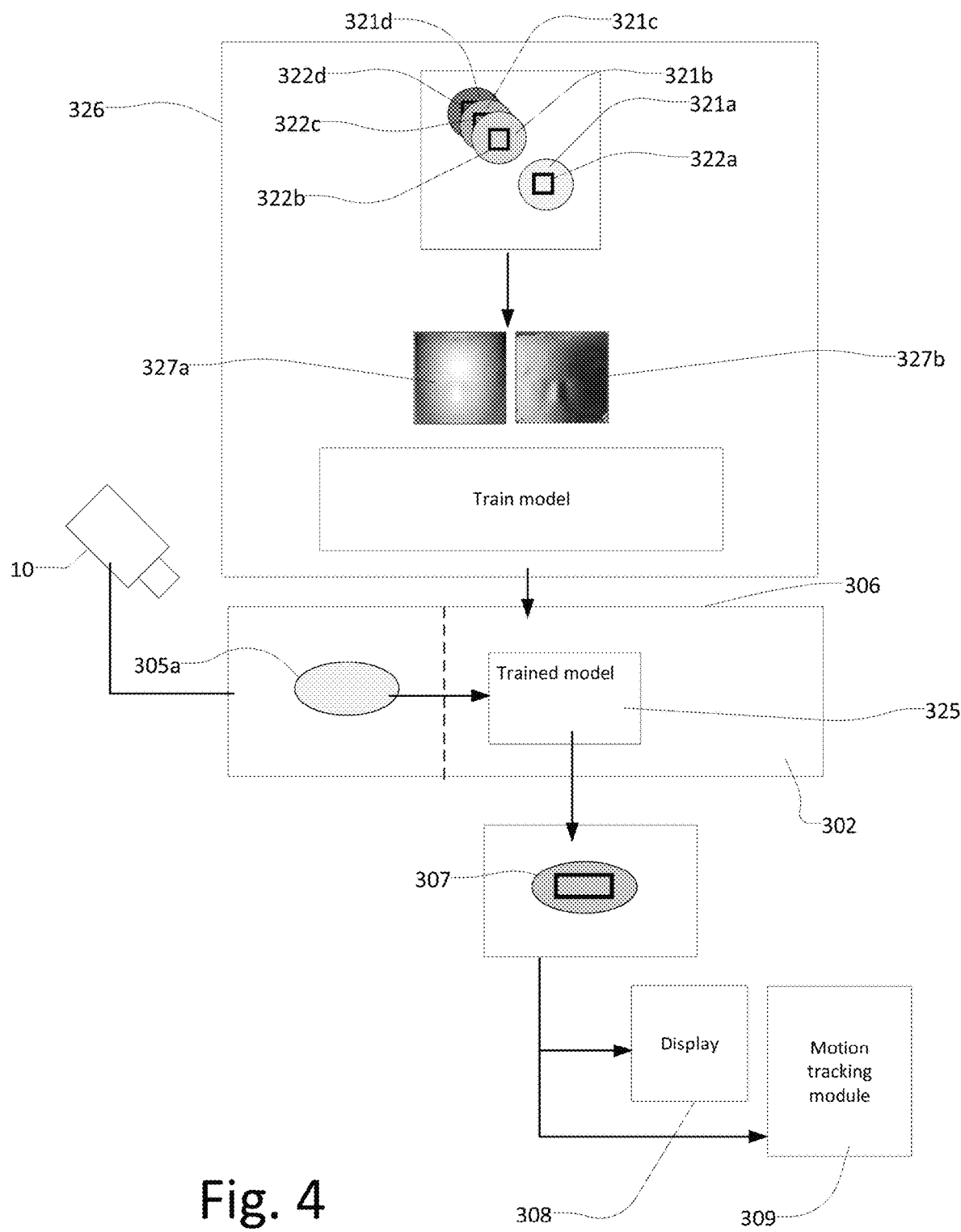
FIG. 4 show a schematic illustration of the patient motion tracking system according to a third example for automatic generation of a ROI on a 3D surface.

Another embodiment of the system is illustrated in FIG. 4, where it should be noted that the general features described in relation to FIG. 1 applies. Thus, the main difference of the system will only be elaborated on in further detail. The embodiment of FIG. 4 illustrates a patient motion tracking system according to FIG. 1, wherein the ROI generation module 306 is configured with a trained ROI model 325. Accordingly, in this embodiment, the ROI descriptive data is configured as the ROI model 325. The ROI model 325 is trained in a machine learning processor, i.e. a training module 326, prior to being stored in the memory 302 of the ROI generation processor 306 or alternatively another unit or module of the system. Thus, the system may be configured with the training module itself or may be configured to store a pre-trained ROI model only. In the latter case, the pre-trained ROI model would be generated in another system, and then stored in the patient motion tracking system.

In more detail, the ROI model 325 is trained based on the one or more reference surfaces 321*a*, 321*b*, 321*c*, 321*d* each having an annotated reference ROI 322*a*, 322*b*, 322*c*, 322*d* applied thereto. Thus, it should be understood that in all of the embodiments described herein, the reference surfaces and reference ROIs are utilized as a training data for generating ROI models and/or ROI templates and surfaces used as input to the memory of the ROI generation processor. It should be noted that the training module may be configured as a neural network.

In more detail, the reference surfaces in the training module 326 is in the embodiment shown configured as depth map and normal map surface representations of the input surface. That is, in the embodiment illustrated in FIG. 4, the reference surfaces 321*a*, 321*b*, 321*c*, 321*b* may be configured as a depth map 327*a* and a normal map 327*b* of the surfaces used for training of e.g. a neural network. It should be noted that only one depth map 327*a* and one normal map 327*b* is shown for illustrative purposes, but the training procedure would involve utilizing a plurality of reference surfaces with a depth map and normal map for each reference surface. Accordingly, the model can in one embodiment be trained in the training module 326 on the basis of the just described data, however, other suitable data for training could be contemplated as well. The data used for training should be any suitable data creating a representative way of describing the target surface of the patient and the ROI of interest of the given physical region of the patient, such as the head, abdominal region, arms, legs, etc.

In the embodiment of FIG. 4, the ROI generation processor is in a similar manner as previously described, configured to utilize the 3D surface 305*a*, in this case, as input to the ROI model 325 (configured as a trained neural network), and to output a ROI labelled 3D surface 307 to the display 308 and/or the motion tracking module 309 and/or as previous described (not shown) a quality module.

In more detail, the trained model 325 is stored in and utilized by the ROI generation processor 306 so as to generate the ROI labelled 3D surface 307. This is done by inputting the 3D surface 305*a* to the ROI model 325, which model 325 is configured to classify via the model depth map and normal map representations, vertices of the 3D surface 305*a* as being inside or outside of the region of interest as defined by the trained model. Thus, it should be understood, that the trained model contains a feature representation of the region of interest and a feature representation of a surface relating to such region of interest. In this way, the 3D surface as input to the model can be classified on the basis of these feature representations, and on the basis of the classification, the model is configured to output a suitable ROI label to the 3D surface input to the model.

In an embodiment of FIG. 4, the trained model 325 may be a machine learning model configured as a convolutional neural network, with the convolutions being applied over the 3D surface by defining a local 2D coordinate system for each point on the 3D surface and locally resampling the surfaces in alignment with the convolution kernel, and wherein the output of the model is a classification of points as being inside or outside of the region of interest as defined by the trained model. In a more detailed embodiment, the convolutions may be applied over a mesh of the 3D surface by defining a local 2D coordinate system for one or more vertex on the 3D surface. In this way, the output of the model is a classification of vertices as being inside or outside of the region of interest as defined by the trained model. In more detail a mesh may be configured as a point cloud where points of the point cloud are used to define faces, for instance triangles or quads (quadrangles). It should be noted that this description is just one suitable way of using data to create the model. Other suitable approaches should be contemplated to fall within the scope of the disclosure.

Furthermore, in another example embodiment according to FIG. 4, a feature vector may be computed for each point of the reference surfaces as a description of their local neighborhood in terms of geometry or texture, wherein these features are used as input for the machine learning model to classify each point as being inside or outside the region of interest as defined by the model.

Figure 5:
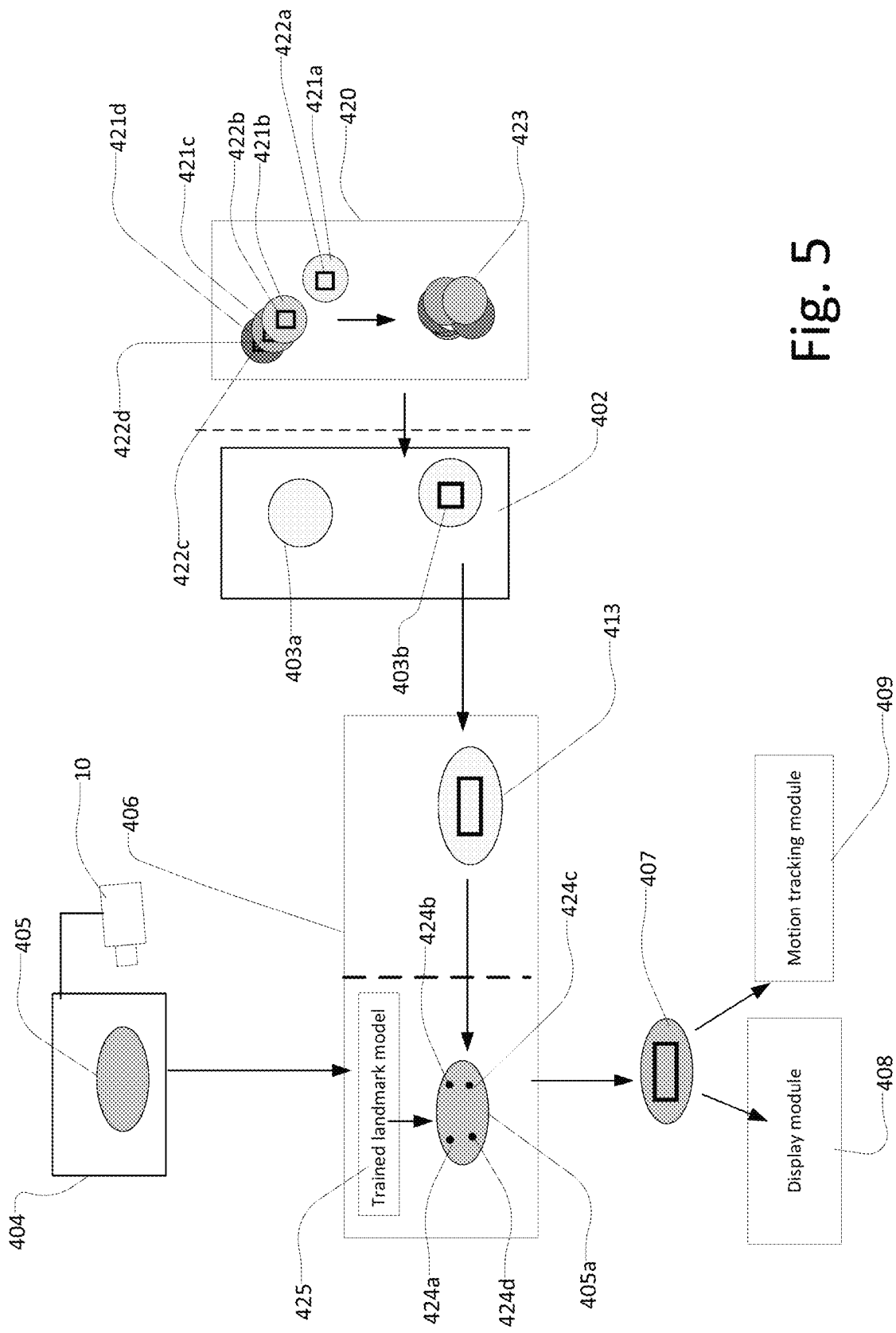
FIG. 5 show a schematic illustration of the patient motion tracking system according to a fourth example for automatic generation of a ROI on a 3D surface.

In yet another embodiment, the motion tracking system is configured to utilize a combination of features of the previously described systems to automatically generate a ROI labelled 3D surface. Such embodiment is illustrated in FIG. 5, where it is illustrated how a trained model 425 as described in relation to FIG. 4 can be utilized to e.g. generate a set of input landmarks to be applied to the 3D surface 405*a*. Thus, instead of a clinician annotating the input landmarks 424*a*, 424*b*, 424*c*, 424*d*, as described in relation to FIGS. 2 and 3, the trained landmark model 425, can be utilized to identify the relevant input landmarks 424*a*, 424*b*, 424*c*, 424*d* in the 3D surface 405*a*, which are used by the ROI generation processor 406 as described in relation to FIGS. 2 and 3.

Thus, in more detail, in the embodiment of FIG. 5, the ROI generation processor 406 comprises a landmark generation model 425, wherein the landmark generation model 425 is trained in e.g. a machine learning processor prior to being stored in the ROI generation processor 406. The landmark generation model 425 is for example trained on the basis of the one or more reference target surfaces 421*a*, 421*b*, 421*c*, 422*b* each having annotated landmarks. In this embodiment, the annotated reference ROIs used in accordance with the description of FIGS. 2 and 3 are denoted 422*a*, 422*b*, 422*c*, 422*d*. Thus, the main difference between the embodiment of FIG. 4 and the embodiment of FIGS. 2 and 3, is only that the input landmarks is automatically found by use of a trained model. The training module 420 is in correspondence with the description of the training module 120, 220 of FIGS. 2 and 3, and reference is made to the description thereof.

Accordingly, in this embodiment, the landmark generation model 425 is configured to output a representation of input landmarks 424*a*, 424*b*, 424*c*, 424*d*, onto the 3D surface 405*a*, thereby creating a landmark labelled 3D surface. The landmark labelled 3D surface 405*a* is then utilized in the ROI generation processor 406 together with the template surface 403*a* and the template ROI 403*b* to align and warp the template ROI 403*b* and template surface 403*b* with the landmark labelled 3D surface 405*a* to create an aligned and warped ROI 413. The aligned and warped ROI 413 is then transferred to the 3D surface 405*a* to output the ROI labelled 3D surface 407. It should be noted that the template ROI 403*b* and template surface 403*a* may be generated in a training module 420 as described in relation to FIGS. 2 and 3—details thereof in view of FIG. 5 is therefore found in the description of FIGS. 2 and 3. Furthermore, the 3D surface 405*a* is generated from an input surface 405 in a 3D surface generator 404 as also described in the previous embodiments.

As already indicated, the combined method described in relation to FIG. 5 creates a fully automated ROI generation system, where there is no need for any user inputs, as achieved by utilizing a trained landmark model to identify in the 3D surface the landmarks needed for the ROI generation processor to identify from the stored ROI template a suitable ROI for motion tracking by the motion tracking module 409. Furthermore, and in accordance with all the embodiments described herein, this 3D labelled ROI surface can be evaluated by a user (via a display 408) and/or automatically by the system by utilizing a ROI quality module, as previously described.

Figure 6:
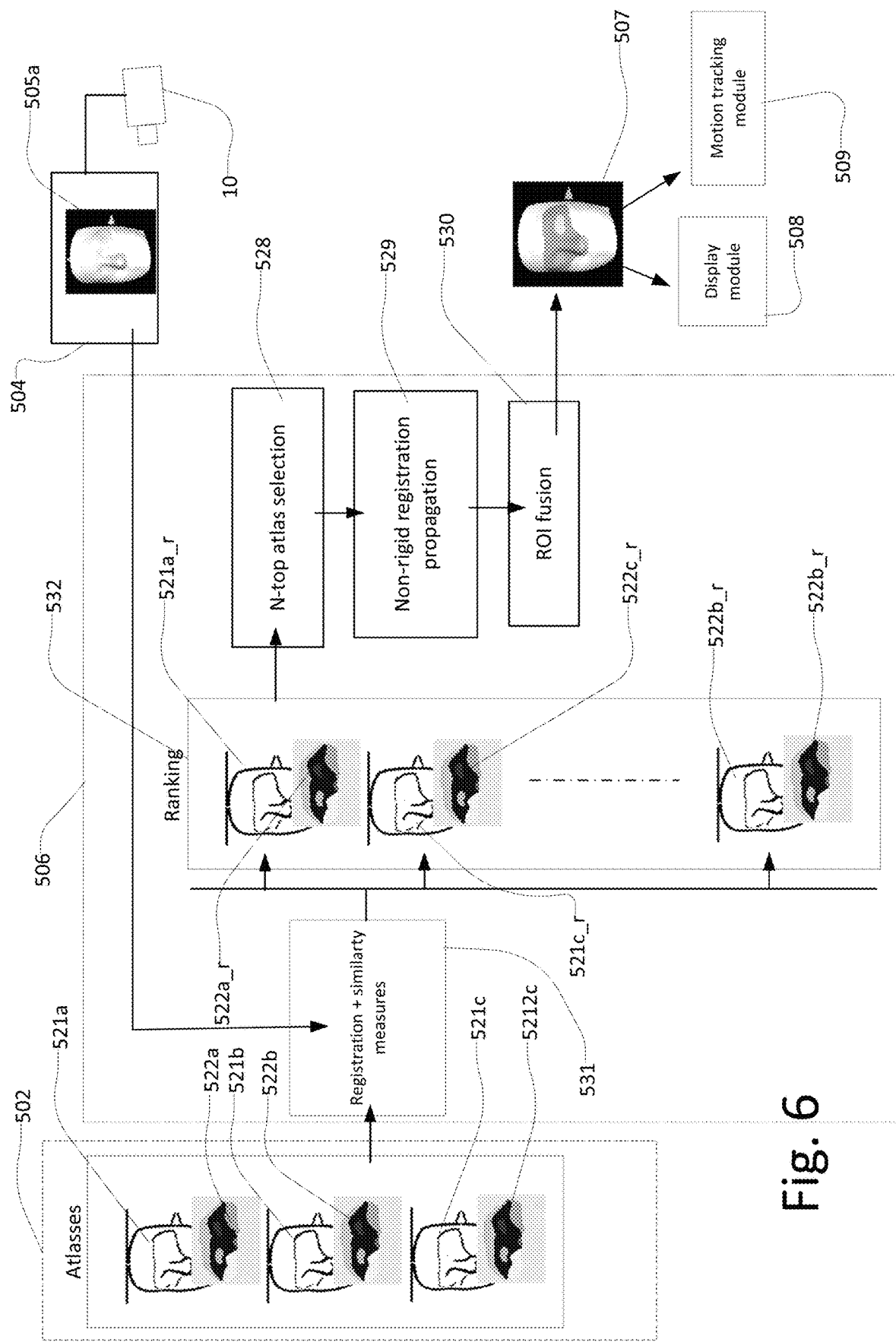
FIG. 6 show a schematic illustration of the patient motion tracking system according to a fifth example for automatic generation of a ROI on a 3D surface.

In a further embodiment illustrated in FIG. 6, the ROI generation processor 506 is configured to utilize another method than the previously described to automatically generate a ROI labelled 3D surface of the input 3D surface. Accordingly, and as illustrated in FIG. 6, the system is configured with a memory 502 comprising a set of reference surfaces 521*a*, 521*b*, 521*c* each having an annotated reference ROI 522*a*, 522*b*, 522*c* applied thereto, in correspondence with the previously described embodiments. These reference surfaces and reference ROIs represents a set of ROI descriptive atlases, which are stored in the memory 502 and utilized as input to the ROI generation processor 506.

Accordingly, when a 3D surface 505*a* of the patient is input to the ROI generation processor 506, the 3D surface image 505*a* is input into a registration and similarity measure module 531, which also takes as input the set of reference ROIs and reference surfaces from the memory 502. The registration and similarity measure module 531 are configured to perform a registration and similarity measure between the 3D surface 505*a* and the reference ROIs and reference surfaces so as to output a ranking 532 of the reference surfaces 521*a* r, 521*br*, 521*c_r* and their corresponding reference ROIs 522*a* r, 522*b* r, 522*c* r in relation to the 3D surface 505*a* input to the ROI generation processor 506. From the rankings 532, the ROI generation processor 506 is configured to select the N-closest reference surfaces and their corresponding ROIs 528 to the 3D surface 505*a*.

In the illustrated example, the features used in the atlases of the memory to compute similarity measures with the input surface 505*a*, are illustrated as being the reference ROIs and reference surfaces. However, further features, such as sex, height, weight, age, shape descriptors related to the target region of the patient could be used as descriptive features for ranking and selecting these atlases. One or more of such features could be utilized alone or in combination with the examples shown in FIG. 6.

When the N-closest reference surfaces, with their respective ROIs having been identified 528, the ROI generation processor is configured to perform a registration 529 (i.e. a non-rigid registration) between the N-closest examples 528 and the 3D surface 505*a*. The ROIs of the registered atlases are then utilized by a ROI fusion module 530 of the ROI generation processor to create the ROI labelled 3D surface 507 to be output to the display module 508 and the motion tracking module 509. In more detail, a parallel exist between the template approach (i.e. FIGS. 2 and 3) and the atlas approach (FIG. 6), in that each of the N-top selected atlas can be considered as a template. Each of these templates defines a ROI for the input surface, and the ROI fusion modules combines those multiple ROIs into a single ROI, for instance by majority voting.

The embodiment described in relation to FIG. 6 is thus another approach of automatically generating a ROI label to the 3D surface of the patient. In the illustration of FIG. 6, the procedure and system is illustrated in an SRS setup, but could be utilized in any suitable radiotherapy treatment system having the target area being specified around other parts of a patient body. The important feature for all of the embodiments described herein is that the "training data" either stored in a memory directly or trained remote from the system, as such, is based on a suitable representation of the part of the patient being treated with radiation therapy.

It should be noted that in the embodiments described herein processors and module are described. These processors and/or module may be configured as one or more computer readable mediums. Thus, the functions may be stored on or encoded as one or more instructions or code on a tangible computer-readable medium. The computer readable medium includes computer storage media adapted to store a computer program comprising program codes, which when run on a processing system causes the data processing system to perform at least some (such as a majority or all) of the steps of the method described above, in the and in the claims.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

Furthermore, a data processing system and/or a generation module may comprise a processor adapted to execute the computer program for causing the processor to perform at least some (such as a majority or all) of the steps of the system configurations described above and in the claims.

It is intended that the structural features of the devices described above, either in the detailed description and/or in the claims, may be combined with steps of the configuration of the system, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein but are to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A patient motion tracking system for automatic generation of a region of interest on a 3D surface of a patient positioned in a radiotherapy treatment room, the system comprising:
    a memory comprising stored region of interest (ROI) descriptive data;
    a 3D surface generation processor configured to
        utilize an input surface, and
        generate a 3D surface from said input surface, wherein the 3D surface comprises at least a target area of the input surface;
    a ROI generation processor configured to
        utilize said stored ROI descriptive data and said 3D surface to output a ROI labelled 3D surface to a display and a motion tracking module, wherein said ROI labelled 3D surface is utilized by the motion tracking module to track motion of a patient during positioning and/or treatment of said patient in the treatment room.

2. System according to claim 1, wherein the system comprises a 3D scanning reconstruction system configured to be arranged in the radiotherapy treatment room and configured to generate said input surface.

3. System according to claim 2, wherein the stored ROI descriptive data comprises one or more reference surfaces each having an annotated reference ROI applied thereto.

4. System according to claim 2, wherein said ROI labelled 3D surface is configured to be input to said display, wherein said display is configured to allow a user to adjust said region of interest via control inputs to the ROI generation processor, wherein the control inputs utilizes an adjustment of at least the borders of the ROI label of the ROI labelled 3D surface.

5. System according to claim 1, wherein the input surface is configured as a series of 2D image frames of at least said target area of said patient and said 3D surface generation processor is configured to generate from said 2D image frames said 3D surface.

6. System according to claim 5, wherein the system furthermore comprises one or more cameras configured to be arranged in the radiotherapy treatment room and to obtain said series of 2D image frames of at least the target area of the patient.

7. System according to claim 6, wherein the stored ROI descriptive data comprises one or more reference surfaces each having an annotated reference ROI applied thereto.

8. System according to claim 5, wherein the stored ROI descriptive data comprises one or more reference surfaces each having an annotated reference ROI applied thereto.

9. System according to claim 1, wherein the stored ROI descriptive data comprises one or more reference surfaces each having an annotated reference ROI applied thereto.

10. System according to claim 9, wherein the annotated reference ROI is based on the identification of one or more landmarks applied to each of reference surfaces, wherein the landmarks represent uniquely identifiable portions of the reference target area surface.

11. System according to claim 9, wherein the ROI descriptive data is configured as a ROI model, which ROI model is trained in a machine learning processor prior to being stored in said memory, wherein the ROI model is trained on the basis of said one or more reference target surfaces each having an annotated reference ROI applied thereto.

12. System according to claim 11, wherein the ROI generation processor is configured to utilize the 3D surface as input to said ROI model, and to output said ROI labelled 3D surface to said display and/or said motion tracking module.

13. System according to claim 11, wherein said reference surfaces are configured as depth map and normal map representations of the reference surfaces, and wherein the ROI model is configured to utilize the 3D surface and to classify in said depth map and normal map representations, vertices as being inside or outside of the region of interest as defined by the trained model.

14. System according to claim 9, wherein said ROI generation processor furthermore comprises a landmark generation model, wherein said landmark generation model is trained in a machine learning processor prior to being stored in said ROI generation processor, wherein the landmark generation model is trained on the basis of said one or more reference target surfaces each having annotated landmarks applied thereto.

15. System according to claim 14, wherein the landmark generation model outputs a representation of landmarks onto the input surface, thereby creating a landmark labelled 3D surface, wherein the landmark labelled 3D surface is utilized in said ROI generation processor together with a template surface and a template ROI to
    align and warp said template ROI and template surface with the landmark labelled 3D surface to create an aligned and warped ROI, and
    subsequently to transfer said warped ROI to said 3D surface to output the ROI labelled 3D surface.

16. System according to claim 1, wherein said ROI labelled 3D surface is configured to be input to said display, wherein said display is configured to allow a user to adjust said region of interest via control inputs to the ROI generation processor, wherein the control inputs utilizes an adjustment of at least the borders of the ROI label of the ROI labelled 3D surface.

17. System according to claim 1, wherein said ROI labelled 3D surface is read into a quality module of said system, wherein said quality module is configured to estimate one or more geometric measurements of the 3D data in said ROI labelled 3D surface and to compare said estimated geometric measurements with one or more set thresholds.

18. System according to claim 1, wherein the ROI descriptive data comprises
- a template surface and
- a template ROI,
- wherein said template surface and template ROI are input to said ROI generation processor, which is configured to
- align and warp said template ROI and template surface with the 3D surface to create at least a warped ROI, and
- subsequently to transfer said warped ROI to said 3D surface.

19. System according to claim 18, wherein the system furthermore comprises a training module configured to generate and output to said memory, the template surface and the template ROI.

20. System according to claim 19 wherein said training module comprises two or more reference target surfaces each having an annotated reference ROI applied thereto, wherein the training module is configured to
- align the two or more reference surfaces and subsequently to calculate an average of said aligned reference surfaces to produce said template surface, and
- calculate an average of said annotated ROIs to produce said template ROI.

* * * * *